(12) United States Patent
Craige, III et al.

(10) Patent No.: US 9,091,718 B2
(45) Date of Patent: Jul. 28, 2015

(54) TESTING ELECTRICAL CONNECTIONS BETWEEN CARDIAC RESUSCITATION DEVICES AND EXTERNAL ELECTRODES

(75) Inventors: David N. Craige, III, Attleboro, MA (US); Pisit Khuon, Johnston, RI (US)

(73) Assignee: ZOLL Medical Corporation, Chelmsford, MA (US)

( * ) Notice: Subject to any disclaimer, the term of this patent is extended or adjusted under 35 U.S.C. 154(b) by 209 days.

(21) Appl. No.: 13/613,887

(22) Filed: Sep. 13, 2012

(65) Prior Publication Data

US 2013/0113496 A1 May 9, 2013

Related U.S. Application Data

(60) Provisional application No. 61/535,161, filed on Sep. 15, 2011.

(51) Int. Cl.
*A61N 1/04* (2006.01)
*G01R 31/04* (2006.01)
*A61B 5/0408* (2006.01)

(52) U.S. Cl.
CPC ............... *G01R 31/04* (2013.01); *A61N 1/046* (2013.01); *A61B 5/04085* (2013.01)

(58) Field of Classification Search
USPC .......................... 607/2, 5, 115, 142, 149, 152
See application file for complete search history.

(56) References Cited

U.S. PATENT DOCUMENTS

| | | | |
|---|---|---|---|
| 4,779,630 A | 10/1988 | Scharnberg et al. | |
| 5,462,157 A | 10/1995 | Freeman et al. | |
| 5,579,919 A | 12/1996 | Gilman et al. | |
| 5,645,571 A | 7/1997 | Olson et al. | |
| 5,700,281 A | 12/1997 | Brewer et al. | |
| 5,755,742 A | 5/1998 | Schuelke et al. | |
| 5,817,151 A | 10/1998 | Olson et al. | |
| 5,984,102 A | 11/1999 | Tay | |
| 6,016,059 A | 1/2000 | Morgan | |
| 6,782,293 B2 | 8/2004 | Dupelle et al. | |
| 7,801,605 B2 | 9/2010 | Smirles et al. | |
| 8,005,552 B2 | 8/2011 | Covey et al. | |
| 8,565,901 B2 | 10/2013 | Dupelle et al. | |
| 2002/0082644 A1* | 6/2002 | Picardo et al. | 607/1 |
| 2003/0023274 A1 | 1/2003 | Chesley et al. | |
| 2003/0083729 A1* | 5/2003 | Solosko et al. | 607/142 |
| 2005/0159782 A1 | 7/2005 | Powers et al. | |
| 2005/0277991 A1 | 12/2005 | Covey et al. | |
| 2006/0178706 A1 | 8/2006 | Lisogurski et al. | |
| 2007/0203558 A1 | 8/2007 | Jonsen et al. | |
| 2008/0097546 A1 | 4/2008 | Powers et al. | |

\* cited by examiner

*Primary Examiner* — Allen Porter, Jr.
(74) *Attorney, Agent, or Firm* — Fish & Richardson P.C.

(57) ABSTRACT

Testing integrity of electrical connections between cardiac resuscitation devices and electrodes connected thereto while the electrodes remain stored within a sealed package. Each electrode comprises a skin-contacting gel layer, a current-spreading layer, and an adhesive layer for adhering the electrode to the patient. An electrical lead for delivering a therapy pulse extends from the current-spreading layer of each electrode to the exterior of the package. A jumper element located within the package and connected to the current-spreading layer of each electrode provides a self-test electrical connection between the first and second electrical leads while the electrodes are adhered to a substrate within the package to permit testing the integrity of the electrical connection between the electrodes and cardiac resuscitation device prior to use of the electrodes. The jumper is configured so that the self-test electrical connection is broken when the user removes the electrodes from the substrate.

22 Claims, 8 Drawing Sheets

TESTING ELECTRICAL CONNECTIONS BETWEEN CARDIAC RESUSCITATION DEVICES AND EXTERNAL ELECTRODES

CROSS-REFERENCE TO RELATED APPLICATIONS

This application claims priority to U.S. Application Ser. No. 61/535,161, filed on Sep. 15, 2011.

TECHNICAL FIELD

This invention relates to packaged cardiac therapy electrodes, and particularly to techniques for testing connections between the electrodes and cardiac resuscitation devices.

BACKGROUND

External cardiac resuscitation devices (e.g., defibrillators) deliver current pulses to a patient through a pair of electrodes that are typically adhesively secured to the chest of the patient. Each electrode is connected to the resuscitation device by an electrical cable and at least one electrical connector. Often, two electrical cables and two electrical connectors are used. One cable extends from a first connector at the defibrillator to a second connector in the vicinity of the patient. A second cable, which is typically supplied as an integral part of the electrode, makes the connection from the second connector to the electrode. The two defibrillation electrodes are typically disposable, and come sealed within a package. To reduce the time required to deliver defibrillation therapy, the electrodes are often connected to the defibrillator ahead of time.

For a variety of reasons, the prior art has suggested providing an electrical connection between the electrodes within the interior of the electrode package used with cardiac resuscitation devices. One approach (U.S. Pat. No. 5,579,919) has been to provide an electrical connection between the gel layers of the electrodes, e.g., by adhering the two electrodes to an electrically conductive release liner. The purpose for this connection has been to determine the integrity of the electrode (e.g., whether the gel layers remain moist and properly functioning). The resistance across the two electrodes is monitored, and a rise in resistance is indicative of electrode failure.

Another reason for providing an electrical connection between the electrodes has been to provide a way for the electronics of the defibrillator to determine the state of the rescue effort, and take desired action. It has been suggested (U.S. Pat. No. 5,700,281, U.S. Pat. No. 5,817,151) that a metal strip be connected between the current-spreading layers, and the strip positioned so that when the package is opened the strip is torn to break the connection. That permits the electronics monitoring the short circuit formed by the electrode cables and the metal strip to detect that the strip has been severed, and learn that the electrodes have been removed from the package.

Similarly, a frangible electrical connective link (41, FIG. 16) has been provided (U.S. Pat. No. 7,801,605) between the electrodes, with the frangible link being mechanically connected to the housing of the defibrillator so that when the electrodes are removed from their packaging, or from their normal storage location, the frangible link is broken, and electronics onboard the defibrillator automatically turns on power to the defibrillator.

The present assignee introduced a product in which an additional electrical lead was connected within the package to each of the electrical therapy leads, and the additional electrical leads were brought to a connector installed at the periphery of the package. The connector included a shorting conductor that electrically connected the two additional leads together. The shorting conductor was configured so that when the package was opened according to instructions, the shorting conductor was withdrawn from the connector and remained with the discarded packaging. The electrical connection between the two therapy leads provided by the additional leads and the shorting connector was used to periodically test the integrity of the cables and connectors providing the electrical connection between the defibrillator and the packaged electrodes. But the additional leads were connected to the therapy leads short of the location at which the therapy leads were connected to the current-spreading layer, and so the testing was unable to test the entirety of the connection between the defibrillator and the current-spreading layers. And, furthermore, it was discovered in use of the product that the electrode package could possibly be opened incorrectly in a manner that would not result in the shorting connector being withdrawn, thus leaving the possibility that the electrodes might be applied with the shorting connector still in place.

SUMMARY

In a first aspect, the invention features a packaged pair of cardiac therapy electrodes for use with a cardiac resuscitation device, comprising first and second cardiac therapy electrodes, each electrode comprising a gel layer for making electrical contact with the skin of a patient, a current-spreading layer for spreading current across the area of the gel layer, and an adhesive layer for adhering the electrode to the skin of a patient, a package in which the first and second cardiac therapy electrodes are contained prior to use, a substrate within the package to which the adhesive layer of each of the first and second electrodes is releasably-adhered during storage, first and second electrical leads, one of the leads connected to the current-spreading layer of each of the first and second cardiac therapy electrodes, and each lead extending from one of the electrodes to the exterior of the package, with each lead being configured to deliver a therapy pulse to the electrode when in use, an electrically-conductive jumper element located within the package, connected to the current-spreading layer of each electrode, and providing a self-test electrical connection between the first and second electrical leads while the electrodes are adhered to the substrate within the package to permit testing the integrity of the electrical connection between the electrodes and cardiac resuscitation device prior to use of the electrodes, wherein the self-test electrical connection is made without passing current through either of the gel layers of the electrodes, and wherein the jumper element is configured so that the self-test electrical connection is broken as a consequence of the user removing the electrodes from the substrate.

Preferred implementations of this aspect of the invention may incorporate one or more of the following. The substrate may be a release sheet separate from the package, and wherein the act of peeling an electrode from the release sheet may cause the self-test electrical connection provided by the jumper element to be broken. The substrate may be adhered to the package. At least a portion of the jumper element may remain attached to the substrate after the first and second electrodes have been removed from the substrate. The jumper element may comprise at least one male conductive element engaged with one female conductive element, and wherein the packaged pair of electrodes may be configured to disengage the engaged male element from the female element when the electrodes are removed from the substrate. The jumper element may comprise a first conductor that extends from the connection to the current-spreading layer through an opening in an insulating layer to a disconnection region in which the female and male conductive elements are located. The jumper element may comprise a second conductor that extends from the female and male conductive elements through one or more openings to the substrate to which the electrodes are releasably adhered. The second conductor may be adhered to the substrate, to which it is retained when the male and female conductive elements become disengaged at the disconnection region. The disconnection region may be at a location within the electrode so positioned that after disengagement the male or female element remaining in the disconnection region is covered by layers of insulating material so as not to present a risk to the user when a therapy pulse is delivered to the electrode. Each of the first and second electrodes may have its own engaged male and female conductive elements located in its own disconnection region. No layers of adhesive may impede disengagement of the male and female connective elements in the disconnection region. The jumper element may be connected to the current-spreading layer of each of the first and second electrodes at the same locations as the first and second electrical leads are connected to the current-spreading layers.

In a second aspect, the invention features a method of testing the integrity of the electrical connections between a cardiac resuscitation device and electrodes connected to the device while the electrodes remain stored within a sealed package, the method comprising providing a packaged pair of electrodes comprising first and second cardiac therapy electrodes, each electrode comprising a gel layer for making electrical contact with the skin of a patient, a current-spreading layer for spreading current across the area of the gel layer, and an adhesive layer for adhering the electrode to the skin of a patient, a package in which the first and second cardiac therapy electrodes are contained prior to use, a substrate within the package to which the adhesive layer of each of the first and second electrodes is releasably-adhered during storage, first and second electrical leads, one of the leads connected to the current-spreading layer of each of the first and second cardiac therapy electrodes, and each lead extending from one of the electrodes to the exterior of the package, with each lead being configured to deliver a therapy pulse to the electrode when in use, an electrically-conductive jumper element located within the package, connected to the current-spreading layer of each electrode, and providing a self-test electrical connection between the first and second electrical leads while the electrodes are adhered to the substrate within the package to permit testing the integrity of the electrical connection between the electrodes and cardiac resuscitation device prior to use of the electrodes, wherein the self-test electrical connection is made without passing current through either of the gel layers of the electrodes, and wherein the jumper element is configured so that the self-test electrical connection is broken as a consequence of the user removing the electrodes from the substrate, and testing to determine that an electrical connection exists between the first and second electrical leads at times when the electrodes are stored within the package.

Preferred implementations of this aspect of the invention may incorporate one or more of the following. The substrate may be a release sheet separate from the package, and wherein the act of peeling an electrode from the release sheet may cause the self-test electrical connection provided by the jumper element to be broken. The substrate may be adhered to the package. At least a portion of the jumper element may remain attached to the substrate after the first and second electrodes have been removed from the substrate. The jumper element may comprise at least one male conductive element engaged with one female conductive element, and wherein the packaged pair of electrodes may be configured to disengage the engaged male element from the female element when the electrodes are removed from the substrate. The jumper element may comprise a first conductor that extends from the connection to the current-spreading layer through an opening in an insulating layer to a disconnection region in which the female and male conductive elements are located. The jumper element may comprise a second conductor that extends from the female and male conductive elements through one or more openings to the substrate to which the electrodes are releasably adhered. The second conductor may be adhered to the substrate, to which it is retained when the male and female conductive elements become disengaged at the disconnection region. The disconnection region may be at a location within the electrode so positioned that after disengagement the male or female element remaining in the disconnection region is covered by layers of insulating material so as not to present a risk to the user when a therapy pulse is delivered to the electrode. The first and second electrodes may have its own engaged male and female conductive elements located in its own disconnection region. No layers of adhesive may impede disengagement of the male and female connective elements in the disconnection region. The jumper element may be connected to the current-spreading layer of each of the first and second electrodes at the same locations as the first and second electrical leads are connected to the current-spreading layers.

Among the many advantages of the invention are the following. The invention permits testing of the integrity of the full electrical connection from the cardiac resuscitation device to the current-spreading layer of each of the electrodes. By causing the jumper element to disconnect when the electrodes are removed from the substrate, rather than when the package is opened, the invention is less susceptible to problems occurring when users open the package in unintended ways.

Other features and advantages of the invention will be apparent from the drawings, detailed description, and claims.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
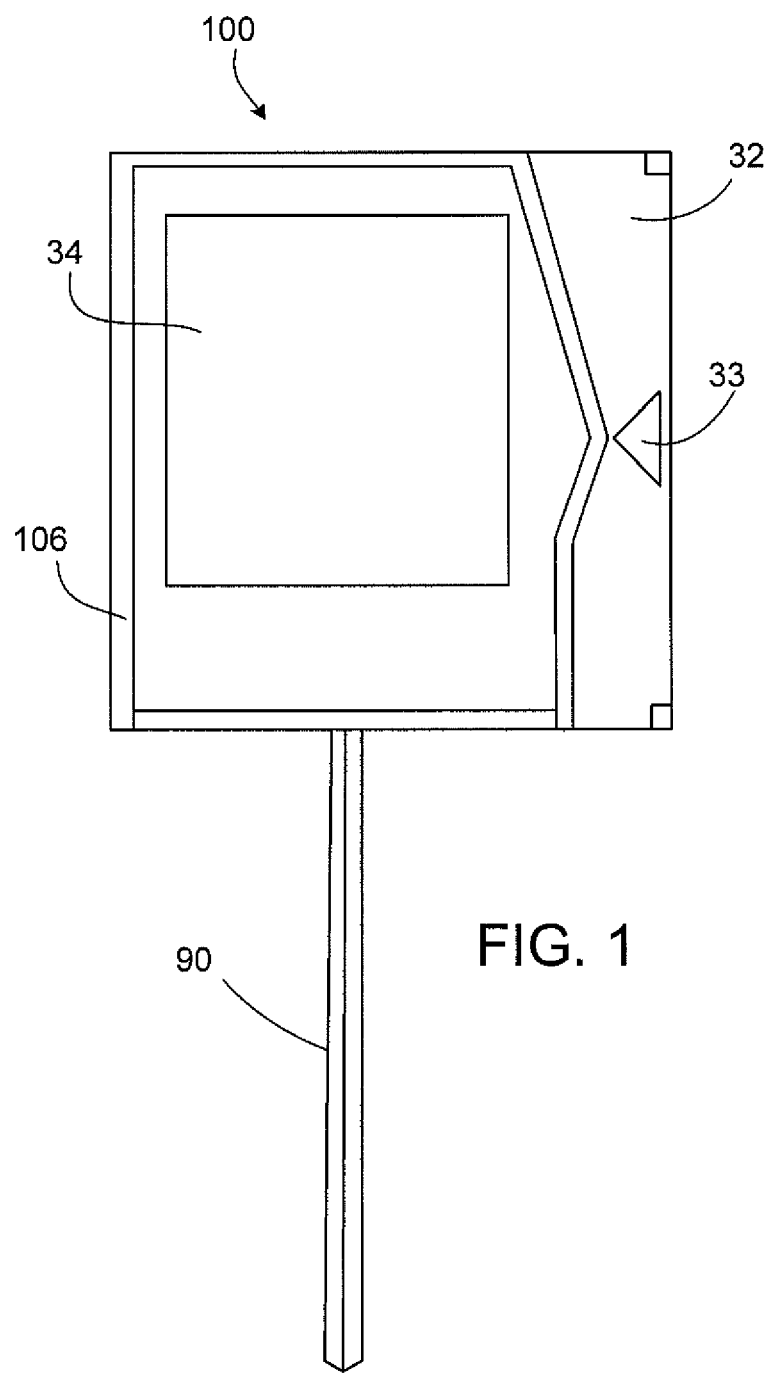
FIG. 1 is a plan view of the exterior of an assembled electrode package.

One implementation of the invention is depicted in FIG. 1, which shows the assembled electrode package 100 with multi-conductor electrical lead 90 and label 34. The package is opened by grasping the loose flaps 32 at arrow label 33, and peeling back the top flap. As the flaps are pulled apart, releasable peripheral adhesive 106 parts.

Figure 2:
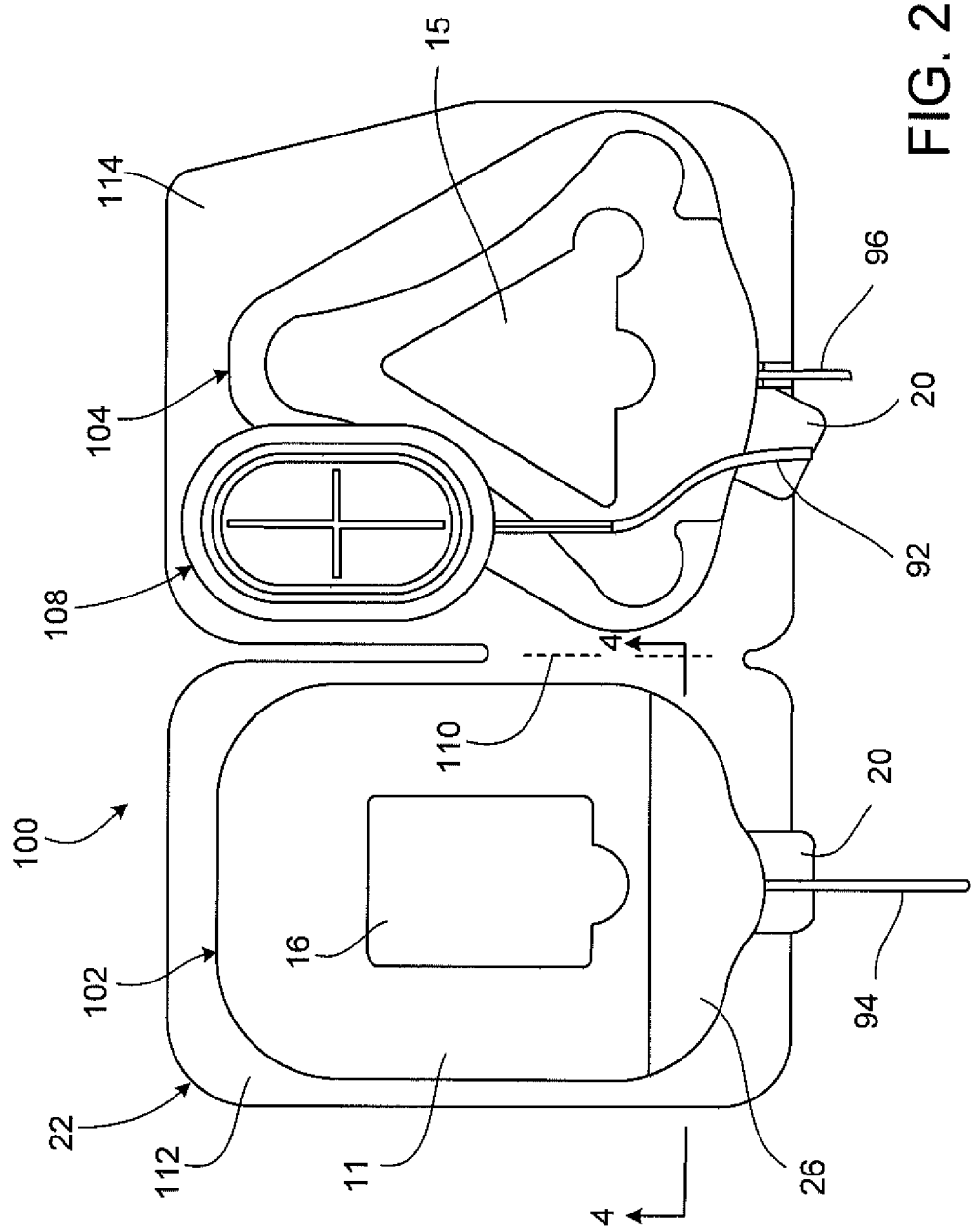
FIG. 2 is a plan view of the contents of the package after opening, showing the two electrodes and accelerometer prior to removal from the styrene sheet.

FIG. 2 shows the electrodes 102, 104, accelerometer 108, and styrene sheet 22 found inside the package. Before the package is opened, the styrene sheet is folded along fold line 110 in the form of a closed book, with the electrodes 102, 104 and accelerometer 108 peelably attached to the interior facing surfaces 112, 114 of the book. On opening the package, the book is unfolded, so that the electrodes and accelerometer are presented to the user as shown in FIG. 2.

Electrode 102 is designed to be peeled from the styrene sheet using tab 20, and applied to the back of the patient's chest. Electrode 104 is peeled using another tab 20, and applied to the front of the chest. Accelerometer 108 is mounted on the same base as electrode 104, and is peeled from the styrene sheet along with the electrode. The accelerometer works with electronics in the defibrillator to determine the depth of compressions during CPR. Three ECG electrodes (not shown) are built into front electrode 104 (each is located at approximately the corners of the triangular shape of the electrode). Labels 15, 16 instruct the user in how to attach the electrodes and accelerometer. Each electrode has a wire lead 94, 96 that extends to a connector (not shown) for connection to the defibrillator. Lead 92 from the accelerometer and leads from the ECG electrodes (not shown) also extend to the same connector (not shown). All of the leads are joined together in one multi-conductor lead 90 (FIG. 1).

Figure 3:
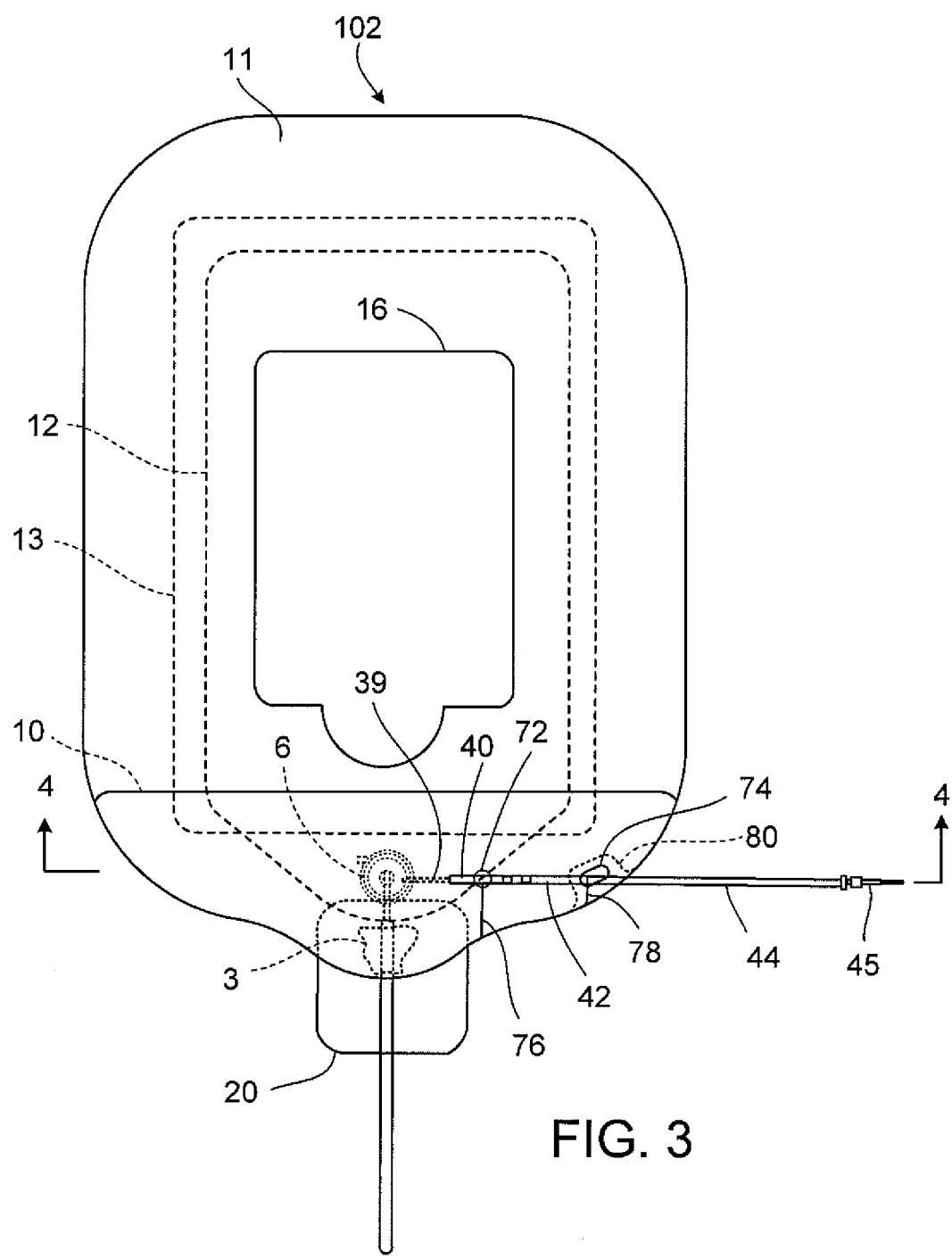
FIG. 3 is a plan view of one of the electrodes.
Figure 4:
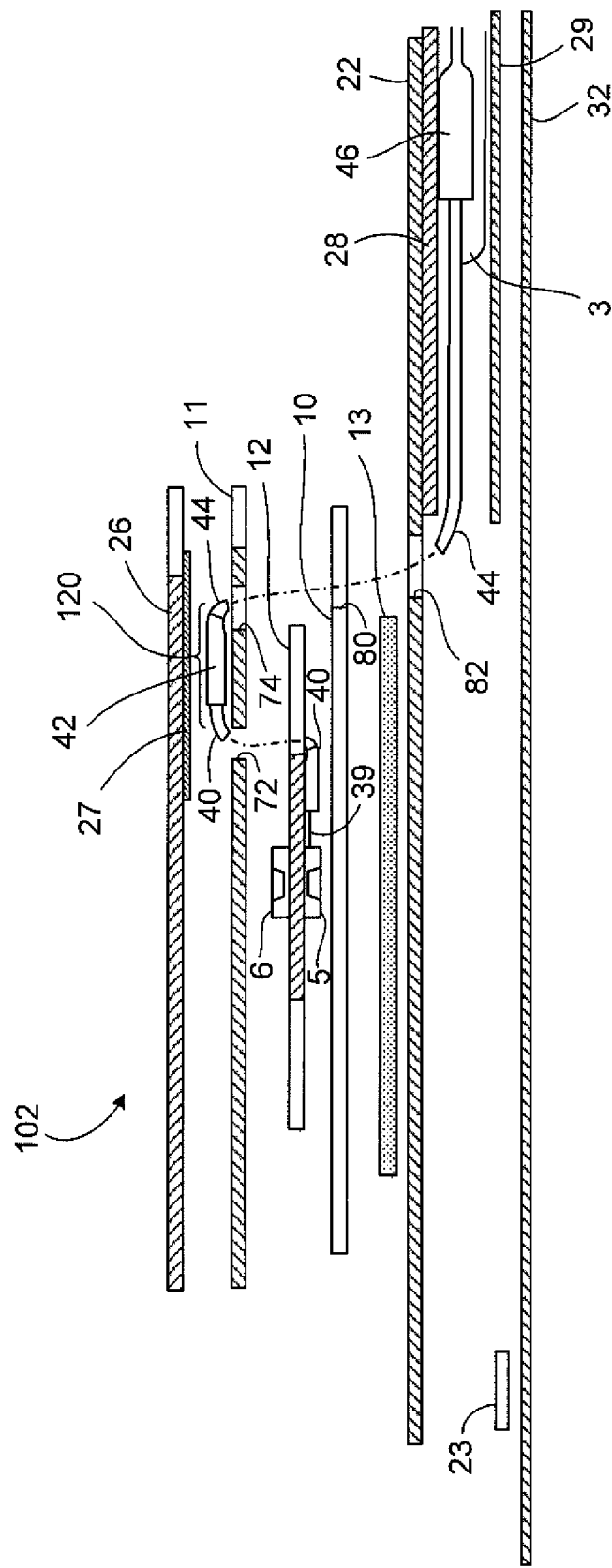
FIG. 4 is a cross sectional, partially exploded view taken along section 4-4 in FIGS. 2 and 3.
Figure 5:
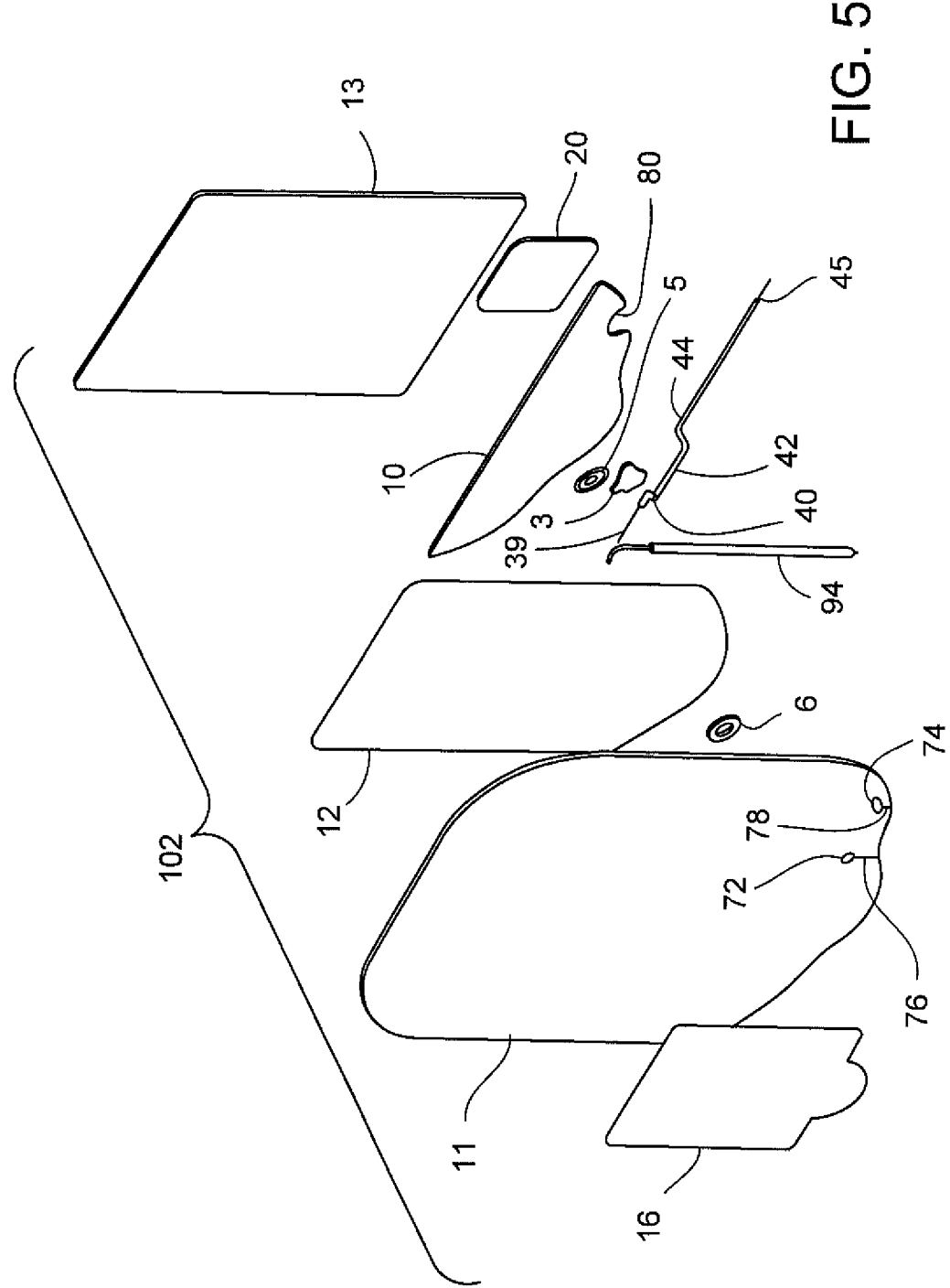
FIG. 5 is an exploded perspective view of the electrode of FIGS. 3 and 4.

FIG. 3 shows the back electrode 102 in plain view, looking down on the upper surface of the electrode on which label 16 is exposed. FIG. 4 is a cross sectional view of the back electrode along section 4-4 in FIG. 3, showing construction of the self-test jumper. FIG. 5 is an exploded view of the back electrode.

Figure 6:
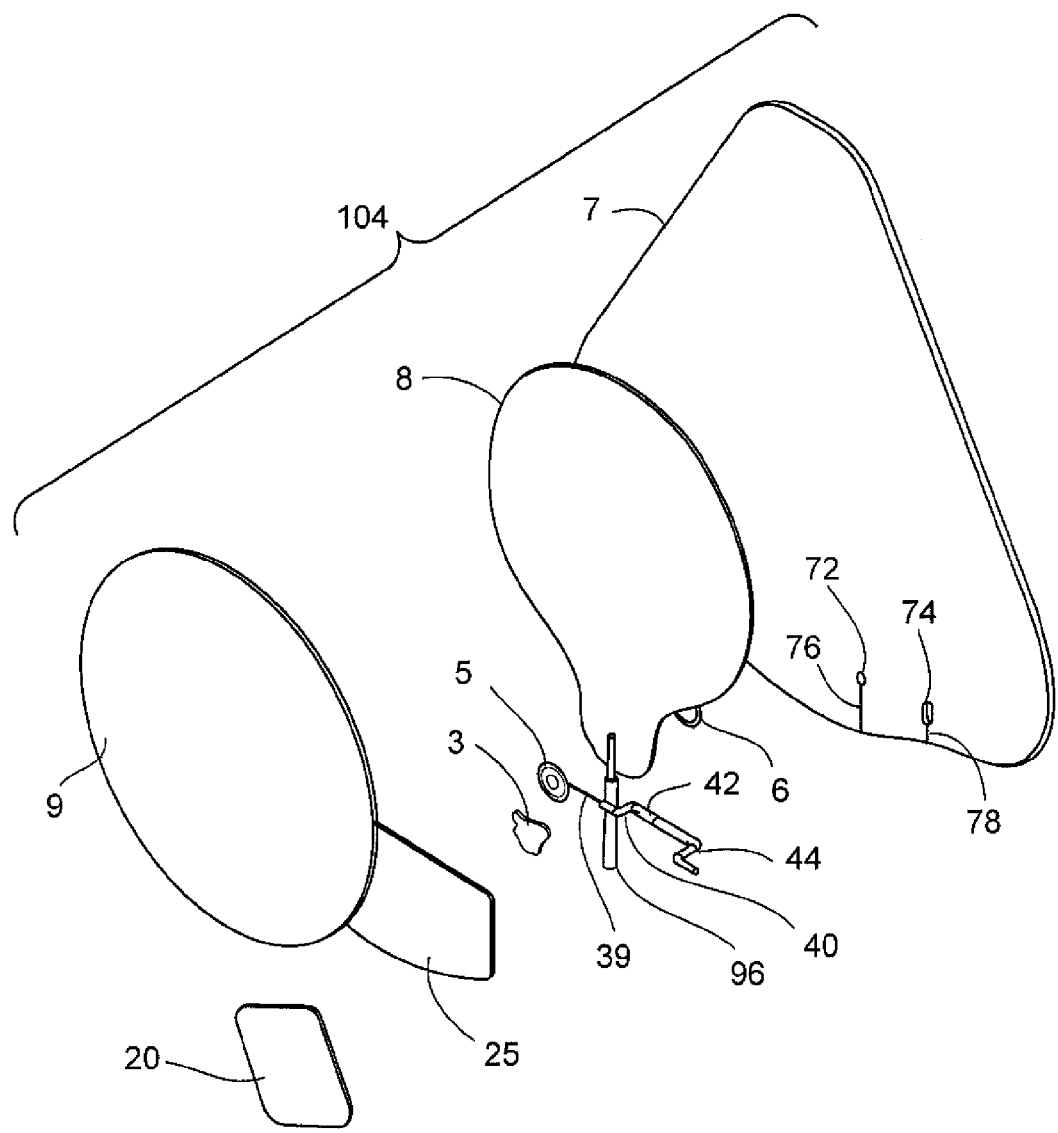
FIG. 6 is an exploded perspective view of the other electrode.

Construction of the front electrode 104 is identical to that of the back electrode 102 in respects relevant to the self-test jumper, hence separate plan and cross-sectional views are not provided. But a separate exploded view of the front electrode is shown in FIG. 6 (which has been simplified to leave out the three ECG electrodes and accelerometer).

FIG. 4 is probably the most helpful for understanding the construction of the electrodes and the self-test jumper. The layers and other elements of the electrodes are shown mostly in exploded view (although some elements are shown in their assembled relationship to other elements). A foam cover 11 (e.g., Volera closed-cell foam) forms the uppermost layer of the electrode, except in the vicinity of the self-test jumper, where a further insulator layer 26 (e.g., Volera closed-cell foam) is adhered over the foam cover 11. Beneath the foam cover is the metallic, current-spreading layer 12 (e.g., tin or silver silver-chloride) that conducts electrical current uniformly across the active area of the electrode. Beneath the metal plate is the solid gel 13 that contacts the patient's skin. A further insulator layer 10 is positioned between the metallic, current-spreading layer and the solid gel in the area of the self-test jumper. Adhesive on the undersides of the foam cover 11 and insulator layer 10, and the natural adhesive quality of the solid gel 12, adhere the electrode to the patient. And prior to use, those same adhesive portions adhere the electrode to the styrene sheet 22. Strips of double-sided tape 23 adhere the styrene book to the interior face of the package 32.

Electrical lead 94, which delivers defibrillation therapy to the patient, is electrically connected to the electrode by a metallic (stainless steel) ring 6 and socket 5 that mechanically crimp the lead to the metal plate 12 during assembly of the electrode. At the same location at which the lead 94 is connected to the metal plate, a self-test jumper is also connected. Bare conductor (tin-plated copper wire) 39 of the jumper is connected in the same crimping operation. Conductor 39 is covered by a heat shrunk insulative covering 40 (e.g., polyolefin, 3M FP-301), and extends outward at approximately right angles to the direction of electrode lead 94. The conductor 39 with insulative covering 40 passes upwardly through opening 72, and then into a disconnection region 120 formed between foam cover 11 and insulator layer 26. In the disconnection region 120, conductor 39 is electrically connected to female socket connector 42, which is covered by insulative covering that is heat shrunk at the far end (right end in FIG. 4) around the socket 42, but left unshrunk at the near end (left end in FIG. 4) so as not to impede disconnection of conductor 39 from socket 42. A layer 27 of non-adhesive film covers the adhesive undersurface of insulative layer 26, to avoid contact of the adhesive undersurface with conductor 39, covering 40, and socket 42, so that the disconnection of the conductor from the socket is unimpeded by the adhesive. Insulated wire 44 extends from socket 42 downwardly through opening 74 in foam cover 11, then through opening 80 in foam insulator 10, and opening 82 in styrene sheet 22.

Insulated wire 44 then continues in the same direction toward the other electrode 104, which has its own self-test jumper, with a nearly identical configuration. For manufacturing convenience, the insulated wired is staked to a pin (not shown), which engages a socket 46, which is connected to a further length of insulated wire 44 leading to electrode 104. This configuration permits each of electrodes 102, 104 to be manufactured separately, and the insulated wires 44 from each to be connected electrically at socket 46 when the electrodes are assembled on styrene sheet 22.

FIG. 5 is an exploded view of electrode 102, and shows with a few exceptions the same elements as shown in FIG. 4. The exceptions are a portion of hot-melt adhesive 3 securing electrode lead 94 to the underside of foam cover 11, and slits 76, 78 extending from openings 72, 74 to the outer edge of the foam cover. The slits simplify manufacturing assembly of the electrode, as the jumper wire can be placed in its desired configuration—extending upwardly through opening 72 and then downwardly through opening 74—without the need to thread the jumper wire through the openings. The jumper wire can simply be slid into position along slits 76, 78.

FIG. 6 is an exploded view of the other electrode 104. The orientation of the electrode in the figure is reversed from that of FIG. 5. In FIG. 6 the solid gel layer 9 making contact with the patient's skin is the uppermost layer, whereas the solid gel layer 13 of FIG. 5 is the lowermost layer. Just as with electrode 102, there is metallic, current-spreading layer 8 above the solid gel, and a foam cover 7 above the current=spreading layer. Electrical lead 96 connects the electrode to the defibrillator. An additional insulator layer 25 is provided between the solid gel and the current-spreading layer in the vicinity of the jumper wire. Other elements of FIG. 6 have identical numbering to the comparable elements of FIGS. 4 and 5. For simplicity, the ECG electrodes typically built into electrode 104 are not shown in the figure; each of three ECG electrodes is positioned in one of the three corners of the triangular foam cover 7.

Figure 7:
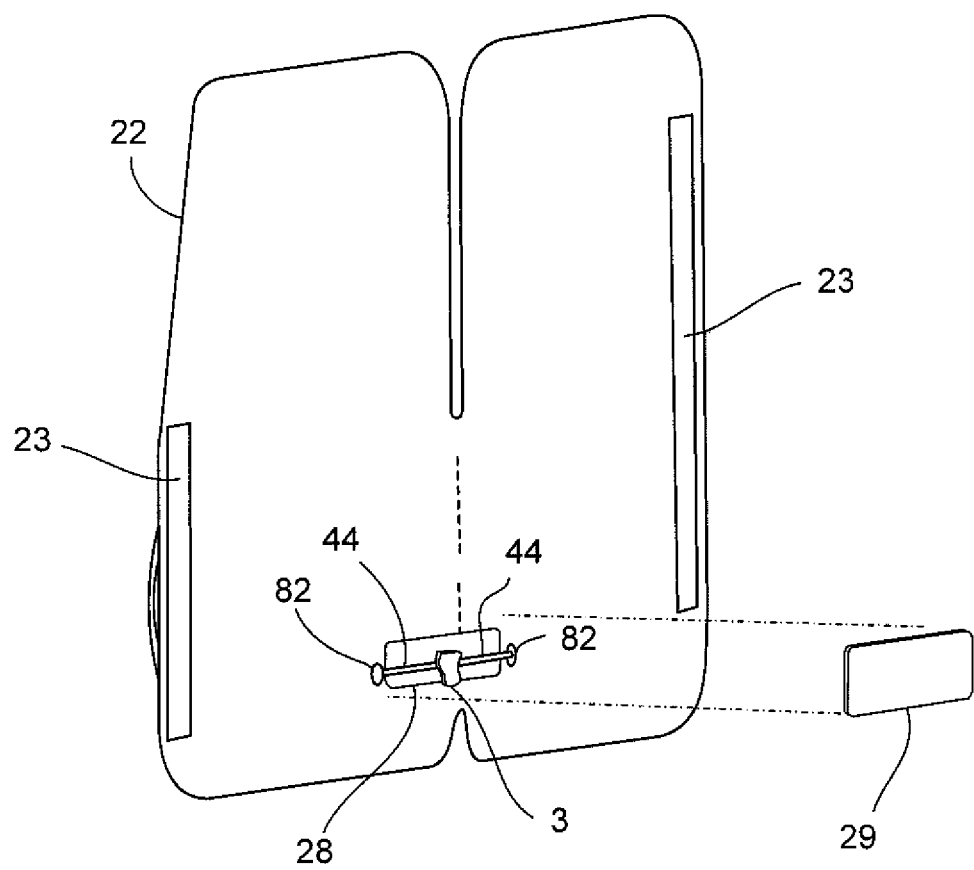
FIG. 7 is a view of the underside of the styrene sheet on which the electrodes are stored inside the package.

FIG. 7 shows the configuration of the self-test jumper on the back surface of the styrene sheet 22. A rectangular piece of foam 28 (e.g., Volera closed-cell foam) with adhesive on both of its surfaces is adhered to the back of sheet 22 along the path followed by the jumper between openings 82. The exposed adhesive and a portion of hot-melt adhesive 3 applied over the jumper helps secure the wire so that it cannot move relative to the styrene sheet. A further rectangular foam strip 29 is secured to the first-mentioned rectangular piece of foam, further securing the jumper to the styrene sheet. Strips of double-sided adhesive tape 23 are provided at opposite edges of the styrene sheet 22 to secure the sheet to the inside surface of the package 32.

Figure 8:
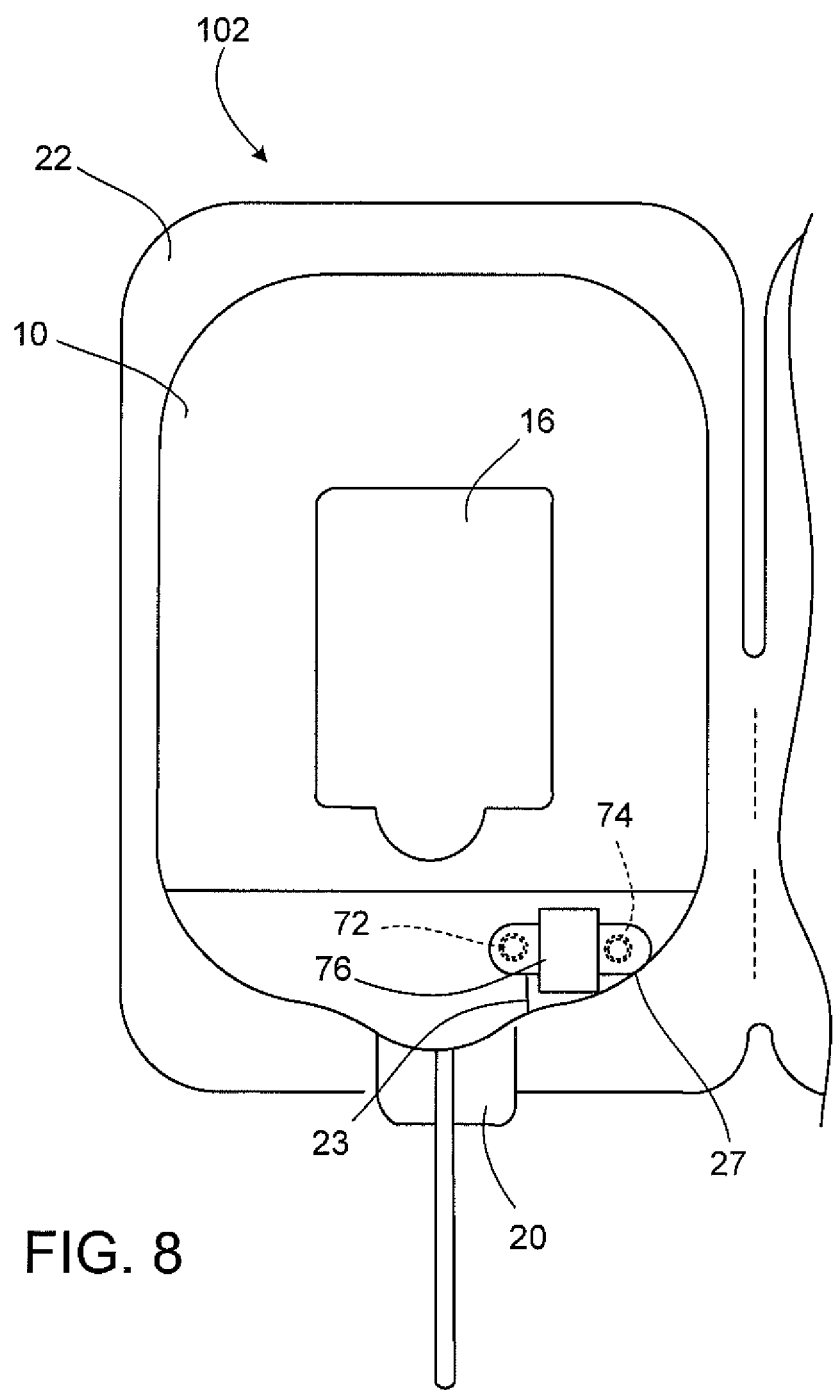
FIG. 8 is a view of the electrode of FIGS. 3-5 at a point during manufacturing.

FIG. 8 shows electrode 102 at a point in time during its assembly. Insulator layer 26 has not yet been adhered to the electrode. A piece of non-adhesive material 27 is applied in disconnection region 120 (FIG. 4), the area across which the self-test jumper extends between openings 72, 74. The material 27 is initially secured in place by a piece of adhesive tape 23, to hold it in the desired orientation over the disconnection region. Then, insulator element 26 is applied over the foam cover. Adhesive on the undersurface of insulator element 26 holds material 27 in place, but the absence of adhesive on the underside of material 27 produces an adhesive-free condition in the disconnection region.

In operation, the self-test jumper (made up of four different connected conductors) provides an electrical connection between the two electrodes 102, 104 while the electrodes are stored inside the electrode package. The jumper provides an electrical connection between the termini of electrical leads 94, 96 at the current-spreading layers 12, 8. This allows self-testing of the integrity of the electrical leads prior to opening the package. Current delivered to one lead 94 should be conveyed to the other lead 96 via the self-test jumper. Failures in the leads, or in the connectors that connect the leads to the defibrillator, can thus be identified.

When the electrodes 102, 104 are removed from the substrate, the self-test jumper is automatically and safely disconnected without the user even being aware of its existence. The disconnection is important, as an electrical short would result upon delivery of the defibrillation pulse across leads 94, 96 if disconnection were not to occur.

The manner in which the self-test jumper is disconnected is as follows. As an electrode is removed (peeled back) from the styrene sheet, the portions of the jumper permanently attached to the electrode (conductor 39, insulative covering 40) disconnects from the portions of the jumper permanently attached to the styrene sheet (socket 42, insulated wire 44). The disconnection takes place in the disconnection region 120, in which there are not adhesive layers or other impediments to relative motion of the portions of the jumper attached to the electrode and portions attached to the styrene sheet. The end of conductor 39—after being disconnected from socket 42—is positioned well inside the structure of the electrode so that no portion of the conductor 39 is exposed. Thus, the fact that a portion of conductor 39 remains with the electrode has no effect on the ability of the electrode to safely deliver electrical therapy to the patient.

Another safety issue addressed by the construction of this implementation is that portions of the self-test jumper that are left attached to the styrene sheet after removal of an electrode are left covered by an insulative covering so that even if a therapy pulse was inadvertently delivered in a manner that supplied the pulse to these portions of the jumper, there would not be a possibility of an exposed conductor coming into contact with the patient or rescuer.

A few of many alternatives to the implementation discussed above and shown in the figures are as follows.

The jumper element could be formed from other conductive materials, e.g., a conductive jumper layer or strip of conductive film could be configured to be in conductive contact with the current-spreading layer of each of the electrodes during storage of the electrodes within the package, and the strip could be secured to the electrode package and configured so that the strip slides out of electrical contact with the current-spreading layer when an electrode is removed from the package.

Disconnection of the jumper element from the electrodes could be achieved by techniques other than disconnecting an electrical wire from an electrical socket, e.g., as just mentioned, by sliding a conductive strip out of contact with the current spreading layer.

The jumper element could be connected to the current-spreading layer at a location other than the location at which the lead delivering the therapy pulse is connected. E.g., the jumper element could be connected to the current-spreading layer at a location distant from the location at which the therapy signal lead is crimped to the layer. One example would be connecting a jumper strip to a tab extending from the current-spreading layer at a location opposite that at which the therapy lead is crimped to the current-spreading layer.

The jumper element could be formed as an integral extension of one or both of the current-spreading layers. E.g., each current-extending layer could be provided with a tab that extends sufficiently to permit the tab from one electrode to overlay and be in electrical contact with the tab extending from the other electrode.

In implementations in which the jumper element includes a conductive jumper layer or strip in electrical contact with the current-spreading layer, a layer of compressible foam could provide sufficient compression to maintain electrical contact between the jumper and current-spreading layers while the electrodes are stored in the package.

Many other implementations of the invention other than those described above are within the invention, which is defined by the following claims.

What is claimed is:

1. A packaged pair of cardiac therapy electrodes for use with a cardiac resuscitation device, comprising
    first and second cardiac therapy electrodes, each electrode comprising a gel layer for making electrical contact with the skin of a patient, a current-spreading layer for spreading current across the area of the gel layer, and an adhesive layer for adhering the electrode to the skin of a patient;
    a package in which the first and second cardiac therapy electrodes are contained prior to use;
    a substrate within the package to which the adhesive layer of each of the first and second electrodes is releasably-adhered during storage;
    first and second electrical leads, one of the leads connected to the current-spreading layer of each of the first and second cardiac therapy electrodes, and each lead extending from one of the electrodes to the exterior of the package, with each lead being configured to deliver a therapy pulse to the electrode when in use;
    an electrically-conductive jumper element comprising at least one male conductive element engaged with one female conductive element, the electrically conductive jumper element located within the package, connected to the current-spreading layer of each electrode, and providing a self-test electrical connection between the first and second electrical leads while the electrodes are adhered to the substrate within the package to permit testing the integrity of the electrical connection between the electrodes and cardiac resuscitation device prior to removal of the electrodes from the package, wherein the self-test electrical connection is made without passing current through either of the gel layers of the electrodes, and wherein the packaged pair of electrodes is configured to disengage the engaged male element from the female element when the electrodes are removed from the substrate so that the self-test electrical connection is broken as a consequence of the user removing the electrodes from the substrate.

2. The packaged pair of cardiac therapy electrodes of claim 1 wherein the substrate is a release sheet separate from the package, and wherein the act of removing an electrode from the release sheet causes the self-test electrical connection provided by the jumper element to be broken.

3. The packaged pair of cardiac therapy electrodes of claim 2 wherein the substrate is adhered to the package.

4. The packaged pair of cardiac therapy electrodes of claim 1 wherein at least a portion of the jumper element remains attached to the substrate after the first and second electrodes have been removed from the substrate.

5. The packaged pair of cardiac therapy electrodes of claim 1 wherein the jumper element comprises a first conductor that extends from the connection to the current-spreading layer through an opening in an insulating layer to a disconnection region in which the female and male conductive elements are located.

6. The packaged pair of cardiac therapy electrodes of claim 5 wherein the jumper element comprises a second conductor that extends from the female and male conductive elements through one or more openings to the substrate to which the electrodes are releasably adhered.

7. The packaged pair of cardiac therapy electrodes of claim 6 wherein the second conductor is adhered to the substrate, to which it is retained when the male and female conductive elements become disengaged at the disconnection region.

8. The packaged pair of cardiac therapy electrodes of claim 1 wherein the disconnection region is at a location within the electrode so positioned that after disengagement the male or female element remaining in a disconnection region is covered by layers of insulating material so as not to present a risk to the user when a therapy pulse is delivered to the electrode.

9. The packaged pair of cardiac therapy electrodes of claim 1 wherein each of the first and second electrodes has its own engaged male and female conductive elements located in its own disconnection region.

10. The packaged pair of cardiac therapy electrodes of claim 1 wherein no layers of adhesive impede disengagement of the male and female connective elements in a disconnection region.

11. The packaged pair of cardiac therapy electrodes of claim 1 wherein the jumper element is connected to the current-spreading layer of each of the first and second electrodes at locations that are the same as locations at which the first and second electrical leads are connected to the current-spreading layers.

12. A method of testing the integrity of the electrical connections between a cardiac resuscitation device and electrodes connected to the device while the electrodes remain stored within a sealed package, the method comprising providing a packaged pair of electrodes comprising
first and second cardiac therapy electrodes, each electrode comprising a gel layer for making electrical contact with the skin of a patient, a current-spreading layer for spreading current across the area of the gel layer, and an adhesive layer for adhering the electrode to the skin of a patient;

a package in which the first and second cardiac therapy electrodes are contained prior to use;

a substrate within the package to which the adhesive layer of each of the first and second electrodes is releasably-adhered during storage;

first and second electrical leads, one of the leads connected to the current-spreading layer of each of the first and second cardiac therapy electrodes, and each lead extending from one of the electrodes to the exterior of the package, with each lead being configured to deliver a therapy pulse to the electrode when in use;

an electrically-conductive jumper element comprising at least one male conductive element engaged with one female conductive element, the electrically conductive jumper element located within the package, connected to the current-spreading layer of each electrode, and providing a self-test electrical connection between the first and second electrical leads while the electrodes are adhered to the substrate within the package to permit testing the integrity of the electrical connection between the electrodes and cardiac resuscitation device prior to removal of the electrodes from the package, wherein the self-test electrical connection is made without passing current through either of the gel layers of the electrodes, and wherein the packaged pair of electrodes is configured to disengage the engaged male element from the female element when the electrodes are removed from the substrate so that the self-test electrical connection is broken as a consequence of the user removing the electrodes from the substrate; and testing to determine that an electrical connection exists between the first and second electrical leads at times when the electrodes are stored within the package.

13. The method of claim 12 wherein the substrate is a release sheet separate from the package, and wherein the act of removing an electrode from the release sheet causes the self-test electrical connection provided by the jumper element to be broken.

14. The method of claim 13 wherein the substrate is adhered to the package.

15. The method of claim 12 wherein at least a portion of the jumper element remains attached to the substrate after the first and second electrodes have been removed from the substrate.

16. The packaged pair of cardiac therapy electrodes of claim 12 wherein the jumper element comprises a first conductor that extends from the connection to the current-spreading layer through an opening in an insulating layer to a disconnection region in which the female and male conductive elements are located.

17. The method of claim 16 wherein the jumper element comprises a second conductor that extends from the female and male conductive elements through one or more openings to the substrate to which the electrodes are releasably adhered.

18. The method of claim 17 wherein the second conductor is adhered to the substrate, to which it is retained when the male and female conductive elements become disengaged at the disconnection region.

19. The method of claim 12 wherein the disconnection region is at a location within the electrode so positioned that after disengagement the male or female element remaining in a disconnection region is covered by layers of insulating material so as not to present a risk to a user when a therapy pulse is delivered to the electrode.

20. The method of claim 12 wherein each of the first and second electrodes has its own engaged male and female conductive elements located in its own disconnection region.

21. The method of claim 12 wherein no layers of adhesive impede disengagement of the male and female connective elements in a disconnection region.

22. The method of claim 12 wherein the jumper element is connected to the current-spreading layer of each of the first and second electrodes at locations that are the same as locations at which the first and second electrical leads are connected to the current-spreading layers.

* * * * *